(12) United States Patent
Foran et al.

(10) Patent No.: US 11,273,044 B2
(45) Date of Patent: *Mar. 15, 2022

(54) METHOD, SYSTEM, AND APPARATUS FOR ANTIBIOTIC DISPENSING KNEE PROSTHESIS

(71) Applicant: ForCast Orthopedics, Inc., Longmont, CO (US)

(72) Inventors: Jared Ruben Hillel Foran, Denver, CO (US); Jeffrey Paul Castleberry, Longmont, CO (US)

(73) Assignee: ForCast Orthopedics, Inc., Longmont, CO (US)

(*) Notice: Subject to any disclaimer, the term of this patent is extended or adjusted under 35 U.S.C. 154(b) by 72 days.

This patent is subject to a terminal disclaimer.

(21) Appl. No.: 16/625,125

(22) PCT Filed: Jun. 22, 2018

(86) PCT No.: PCT/US2018/039040
§ 371 (c)(1),
(2) Date: Dec. 20, 2019

(87) PCT Pub. No.: WO2018/237288
PCT Pub. Date: Dec. 27, 2018

(65) Prior Publication Data
US 2020/0146832 A1    May 14, 2020

Related U.S. Application Data

(60) Provisional application No. 62/524,003, filed on Jun. 23, 2017.

(51) Int. Cl.
*A61F 2/38* (2006.01)
*A61F 2/30* (2006.01)

(52) U.S. Cl.
CPC ............ *A61F 2/389* (2013.01); *A61F 2/3859* (2013.01); *A61F 2002/3068* (2013.01);
(Continued)

(58) Field of Classification Search
CPC .......... A61F 2/389; A61F 2/38; A61F 2/3859; A61F 2002/30672
See application file for complete search history.

(56) References Cited

U.S. PATENT DOCUMENTS

| | | |
|---|---|---|
| 5,344,459 A | 9/1994 | Swartz |
| 5,356,414 A | 10/1994 | Cohen et al. |

(Continued)

FOREIGN PATENT DOCUMENTS

| | | |
|---|---|---|
| CN | 101007184 A | 8/2007 |
| CN | 102133137 A | 7/2011 |

(Continued)

OTHER PUBLICATIONS

Extended European Search Report dated Feb. 16, 2021, including the Supplementary European Search Report and the European Search Opinion, in connection with corresponding EP Application No. 18820016.6 (12 pp.).

(Continued)

*Primary Examiner* — Brian A Dukert
(74) *Attorney, Agent, or Firm* — Maier & Maier, PLLC

(57) ABSTRACT

A spacer for a knee replacement prosthesis may be provided. The spacer may include a lower surface, the lower surface having a locking component adapted to interlock with a tibial tray; an upper surface, the upper surface having an optional central femoral guide and a pair of condyle support platforms, each of the condyle support platforms being disposed on an opposite side of the central femoral guide, each of the condyle support platforms being smooth, the surface of each of the condyle support platforms further (Continued)

having a shallow concavity; and a body incorporating the upper and lower surfaces, the body having a hollow outer portion surrounding an internal reservoir, the body being impermeable to fluid; the body further having one or more ports, each with a channel, each channel extending through the hollow outer portion of the body directing the flow of fluid in and out of the port(s).

7 Claims, 12 Drawing Sheets

(52) U.S. Cl.
CPC .............. *A61F 2002/30672* (2013.01); *A61F 2002/3863* (2013.01); *A61F 2310/00005* (2013.01)

(56) References Cited

U.S. PATENT DOCUMENTS

| 5,681,289 | A | * | 10/1997 | Wilcox | ............... A61B 17/72 604/175 |
|---|---|---|---|---|---|
| 2003/0144742 | A1 | | 7/2003 | King et al. | |
| 2004/0180072 | A1 | | 9/2004 | Tunc et al. | |
| 2004/0199250 | A1 | | 10/2004 | Fell | |
| 2011/0178606 | A1 | * | 7/2011 | Deffenbaugh | ........ A61F 2/3868 623/20.15 |
| 2013/0131816 | A1 | * | 5/2013 | Parisi | ............... A61F 2/389 623/20.29 |
| 2015/0038941 | A1 | | 2/2015 | Nebosky et al. | |
| 2015/0134068 | A1 | | 5/2015 | Leonard et al. | |
| 2015/0238691 | A1 | * | 8/2015 | Boyden | ............... A61F 2/30 604/66 |
| 2016/0113696 | A1 | | 4/2016 | Stalcup et al. | |

FOREIGN PATENT DOCUMENTS

| CN | 203852451 | U | | 10/2014 | | |
|---|---|---|---|---|---|---|
| CN | 104507420 | A | | 4/2015 | | |
| CN | 205626207 | A | | 10/2016 | | |
| EP | 174597 | A2 | | 1/2007 | | |
| WO | 2007/084878 | A1 | | 7/2007 | | |
| WO | 2009/068951 | A2 | | 6/2009 | | |
| WO | 2009/091802 | A3 | | 7/2009 | | |
| WO | 2010/025378 | A2 | | 3/2010 | | |
| WO | 2016/205361 | A1 | | 12/2016 | | |
| WO | WO-2016205361 | A | * | 12/2016 | ............. | A61B 17/80 |
| WO | 2017/017648 | A1 | | 2/2017 | | |
| WO | WO-2017098316 | A1 | * | 6/2017 | ............. | A61F 2/389 |

OTHER PUBLICATIONS

Office Action dated Apr. 2, 2021 in corresponding Chinese Application No. 201880041737.4; 21 pages including English-language translation.

International Search Report and Written Opinion of the International Searching Authority dated Sep. 6, 2018 in corresponding International application No. PCT/US2018/039040; 8 pages.

* cited by examiner

Antibiotic Dispensing Total Knee Arthroplasty Implant

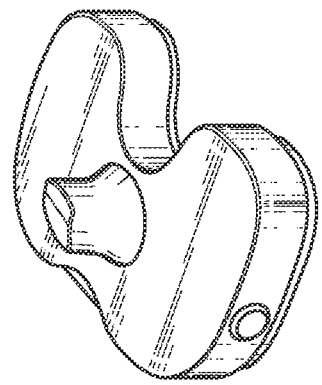

- Hollow Spacer - uses common UHMWPE on exterior surfaces
- Internal Frame - to support the spacer's mechanical performance when hollowed to accommodate a reservoir and infusion system cavity.
- Refill Septum - for replenishment, septum can be imaged via in-office fluoroscopy or ultrasound, or palpated to enable weekly office injections.
- Antibiotic Concentration - consistent therapeutic levels in synovial fluid over period between refills.
- Empty Spacer - after antibiotic therapy is complete, empty spacer meets all industry standards for functioning spacer, eliminating second exchange surgery.

Fig. 8

METHOD, SYSTEM, AND APPARATUS FOR ANTIBIOTIC DISPENSING KNEE PROSTHESIS

PRIORITY CLAIM

This application claims priority to U.S. provisional patent application Ser. No. 62/524,003, filed Jun. 23, 2017, the contents of which are hereby incorporated by reference in their entirety.

BACKGROUND

Though infection is an uncommon complication of arthroplasty, it may have devastating complications, both physical and economic, for a patient. Infection following total knee arthroplasty can be difficult to diagnose and is often difficult to treat once it has been diagnosed. The revision procedure that must be undertaken once an infection has been identified typically involves a combination of surgical debridement to decrease the bacterial bioload as well as prolonged IV and/or oral antibiotics to eliminate the remaining bacteria. This will mean, for the patient, a longer operating time, greater blood loss, and more chance for other complications to arise, along with increases in the total number of hospitalizations of the patient, their duration of hospitalization, their total number of operations, their total hospital costs, and the total outpatient visits and charges that they must endure.

Currently, several options exist for the treatment of an infected total knee arthroplasty. The first option is simple suppression of the infection with intravenous (IV) and/or oral antibiotics. This option is generally reserved for patients that are thought, for any number of reasons, to be unfit for surgery. As a general rule, simple IV and/or oral antibiotic treatment of an infected total knee arthroplasty without concomitant surgery is unlikely to result in eradication of an infection due to the lack of vascularization in the knee and therefore limited transference of the antibiotic from the blood stream to the synovial fluid around the knee. However, IV and/or oral antibiotic treatment may suppress the infection such that it is minimally symptomatic only to reassert sometime after this therapy has been discontinued.

Another option is a so-called "irrigation and debridement and polyethylene exchange." In this procedure, an open irrigation and debridement of the infected knee is undertaken, with concomitant removal of the polyethylene spacer and placement of a new polyethylene spacer (a "polyethylene exchange"). In some instances, surgeons may elect to add dissolvable antibiotic beads into the knee space at the time of surgery for any of these surgical options. Following this procedure, patients are generally placed on at least 6 weeks of IV antibiotics and may then be put on oral antibiotics for an indefinite period of time. An advantage of this procedure is that it preserves the current metallic prosthesis, thus minimizing the morbidity of removing a well-fixed prosthesis. A major disadvantage is that it is difficult to eradicate the infection using this technique. The success rate for eradication of infection varies a great deal, from 31% to 75%. See, for example, S. M. Odum, T. K. Fehring, & A. V. Lombardi, et al., "Irrigation and debridement for periprosthetic infections: does the organism matter?" 26 J. Arthroplasty 6(suppl):114-118 (2011). See also, for example, I. Byren, P. Bejon, & B. L. Atkins, et al., "One hundred and twelve infected arthroplasties treated with 'DAIR' (debridement, antibiotics and implant retention): antibiotic duration and outcome," 63 J. Antimicrob. Chemother. 1264-1271 (2009).

Another option is a so-called "two-stage exchange." A two-stage exchange consists of two operations. In the first operation, the existing prosthesis and surrounding cement are both removed, a thorough irrigation and debridement is performed, and an antibiotic-eluting polymethylmethacrylate (PMMA) ("bone cement") temporary spacer is placed in the knee, in place of the prosthesis. Multiple options for a replacement temporary spacer may exist for this procedure. For example, the temporary spacer may be a static spacer, which consists of a block of PMMA that spans the tibiofemoral space and as such holds the knee in a fixed extended position. The temporary spacer may also be of the articulating variety; in this case, the femoral, tibial, and polyethylene parts of the knee are replaced with antibiotic-impregnated molded PMMA components, which may function as a temporary prosthesis, and which may temporarily elute a high, but diminishing concentration of antibiotics into the knee. This articulating device allows for some movement of the knee joint. There are several commercially available varieties of PMMA articulating spacers, some of which come pre-formed and pre-loaded with antibiotics. (For example, InterSpace Knee, Exactech, Gainesville, Fla., and some of which are molded by the surgeon in the operating room such as, Stage One, Zimmer Biomet, Warsaw, Ind.) Additionally, each of these devices aim to temporarily replace the infected prosthesis. That is, the metal femoral and tibial components are removed and replaced with a temporary femoral and tibial drug delivery implant. Following the first stage, in which the existing prosthesis is replaced with a temporary prosthesis, the patient is placed on at least 6 weeks of IV antibiotics. When the infection is thought to be eradicated, the second stage of the procedure is performed. In this stage, the PMMA temporary spacer is removed, and replaced with a permanent revision prosthesis. The advantage of a two stage procedure is that it has a relatively high success rate, ranging from 72% to 93%. See, for example, S. M. Mortazavi, D. Vegari, A. Ho, B. Zmistowski, & J. Parvizi, "Two-stage exchange arthroplasty for infected total knee arthroplasty: predictors of failure," 469 Clin. Orthop. Relat. Res. 11:3049-54 (November 2011). See also F. S. Haddad, M. Sukeik, & S. Alazzawi, "Is single stage revision according to a strict protocol effective in treatment of chronic knee arthroplasty infections?" 473 Clin. Orthop. Relat. Res. 1:8-14 (January 2015). The disadvantages are the morbidity of two major operations, potential bone loss caused by removal and reimplantation of the prosthesis, and a difficult period for the patient when the antibiotic spacer having restricted functionality is in place.

A fourth option is a so-called "one-stage" or "single-stage" exchange. In one-stage exchange arthroplasty, the infected metal prosthesis is removed, the joint is thoroughly irrigated and debrided, and a new revision prosthesis is put in place (often with antibiotic cement for fixation) all in one operation. This is uncommon in the United States for fear of failure. If this approach is undertaken, generally a large amount of tissue and bone are resected, which is a clear disadvantage.

The success rates for these procedure options are, however, limited, with both undesirable procedures and results for the patients. The use of a temporary antibiotic impregnated cement spacer and impregnated antibiotic beads in the "two stage exchange" procedure, acknowledges the need to direct antibiotic into the effective joint space and the synovial fluid in order to directly treat the bacterial infection at its source. However, the elution of antibiotics from impregnated cement (spacer or beads) is uncontrolled and typically reflects an initial high dosage rate that quickly falls to non-therapeutic levels which likely contributes to the limited, 72%-93% success rate, as shown in Anagnostakos, et al, Elution of gentamicin and vancomycin from polymethylmethacrylate beads and hip spacers in vivo, Acta Orthopadedica 2009; 80 (2); 193-197. Meanwhile, alternate clinical research has demonstrated improved outcomes through direct, daily intraarticular injection of antibiotic over the treatment period. This method intends to maintain a minimum therapeutic level of antibiotic concentration in the synovial fluid above what can be achieved with systemic IV antibiotics and a concentration that is more consistent than what is achieved with an antibiotic impregnated cement spacer over the duration of therapy, typically around 6 weeks. However, while daily patient injections can be managed as part of a clinical study, this approach is intolerable to standard clinical and office practice, and thus highly undesirable for all involved. Also, externally communicating catheters emanating from the joint through tissue to be connected to a pump or syringe for injection represent another potential entry for bacterial infection, which is counter effective to the desired goal. There remains an opportunity for a new device that can achieve consistent and therapeutic levels of antibiotic concentration in the synovial fluid; used in either a temporary or permanent configuration; without the burden of daily injections; without the use of an externally communicating catheter, as a way to improve the success rate of total joint revision for infection.

SUMMARY

According to an exemplary embodiment, methods, systems, and apparatuses involving a spacer for a knee replacement prosthesis may be provided. Such a spacer may include a lower surface, the lower surface having a locking component adapted to interlock with a tibial tray; an upper surface, the upper surface having an optional central femoral guide and a pair of condyle support platforms, each of the condyle support platforms being disposed on an opposite side of the central femoral guide, each of the condyle support platforms being smooth, the surface of each of the condyle support platforms further having a shallow concavity; and a body incorporating the upper and lower surfaces, the body having a hollow outer portion surrounding an internal reservoir, the material of the body being impermeable to fluid; the body further having one or more ports, each with a channel, each channel extending through the hollow outer portion of the body directing the flow of fluid in and out of the port(s). At least one channel can have features to receive fluid into the reservoir, for example a septum or filling tube. At least one channel can have features to exhaust fluid from the reservoir into the synovial fluid, surrounding tissues and vascular bed, e.g. a flow restrictor or diffusor. One channel could be configured for both purposes. Further, the fluid exhausting from the reservoir can be under pressure, whether cyclic or continuous, to overcome any flow restriction that develops in the channel for exhausting fluid due to the buildup of biofilms or interference with surrounding tissue. Further, the body surrounding the hollow reservoir can be configured either as a singular homogenous material or as a multi-component assembly, e.g. a durable cover over a high strength frame forms the nonpermeable body, in order to replicate all of the mechanical, fatigue and wear performance of a solid polyethylene spacer.

In another exemplary embodiment, a total knee prosthesis, used to perform a total knee replacement, may be provided. A total knee prosthesis may include a femoral component having an optional femoral stem adapted to be inserted in an intramedullary canal of a femur, and a pair of condyles; a tibial component having a tibial stem adapted to be inserted in an intramedullary canal of a tibia and hingedly connected to the femoral component, and having a tibial tray; and a spacer, the spacer having a lower surface, the lower surface having a locking component adapted to interlock with the tibial tray; an upper surface, the upper surface having a central femoral guide and a pair of condyle support platforms, each of the condyle support platforms being disposed on an opposite side of the central femoral guide, each of the condyle support platforms being smooth, the surface of each of the condyle support platforms further having a shallow concavity; and a body incorporating the upper and lower surfaces, the body having a hollow outer portion surrounding an internal reservoir, the material of the body being impermeable to fluid; the body further having one or more ports, each having a channel, each channel extending through the hollow outer portion of the body, directing the flow of fluid in and out of the port(s). At least one channel can have features to receive fluid into the reservoir, e.g. a septum or filling tube. At least one channel can have features to exhaust fluid from the reservoir into the synovial fluid, surrounding tissues and vascular bed, e.g. a flow restrictor or diffusor. One channel could be configured for both purposes. Further, the fluid exhausting from the reservoir is under pressure, whether cyclic or continuous, to overcome any flow restriction that develops in the channel for exhausting fluid due to the buildup of biofilms or interference with surrounding tissue. Further, the body surrounding the hollow reservoir can be configured either as a singular homogenous material or as a multi-component assembly, for example a durable cover over a high strength frame forms the non-permeable body, in order to replicate all of the mechanical, fatigue and wear performance of a solid polyethylene spacer; wherein the locking component of the spacer is connected to the tibial tray of the tibial component, and wherein each of the condyles of the femoral component is disposed in one of the condyle support platforms of the spacer. The spacer may be used in a temporary capacity in a two-stage revision procedure, as an articulating, load bearing temporary spacer, ultimately replaced by a permanent spacer after the antibiotic treatment period. Alternatively, the spacer may be used in a permanent configuration, left in place after the antibiotic treatment period and not removed.

In another exemplary embodiment, a method for adding fluid to a spacer for a knee prosthesis may be provided. The spacer may include a lower surface, the lower surface having a locking component adapted to interlock with a separate tibial tray; an upper surface, the upper surface having an optional central femoral guide and a pair of condyle support platforms, each of the condyle support platforms being disposed on an opposite side of the central femoral guide, each of the condyle support platforms being smooth, the surface of each of the condyle support platforms further having a shallow concavity; the upper surface optionally having a locking component adapted to interlock with a separate tibial tray; and a body, the body incorporating the upper and lower surfaces, having a hollow outer portion surrounding an internal reservoir, the material of the body being impermeable to fluid; the body further having one or more ports, each having a channel, each channel extending through the hollow outer portion of the body, directing the flow of fluid in and out of the port in the absence of an external force and permitting the introduction of fluid into the port when an external force is applied. At least one channel can have features to receive fluid into the reservoir, e.g. a port of a septum or filling tube. The method of adding fluid to said spacer may include applying an external force to the port, or septum; inserting a hollow tube or needle into the port or septum; and inserting fluid into the port via the hollow tube or needle. Such a method may be performed percutaneously or otherwise, for example to initially fill the spacer during surgical placement.

In another exemplary embodiment, a method for exhausting fluid from a spacer for a knee prosthesis may be provided. The spacer may include a lower surface, the lower surface having a locking component adapted to interlock with a tibial tray; an upper surface, the upper surface having an optional central femoral guide and a pair of condyle support platforms, each of the condyle support platforms being disposed on an opposite side of the optional central femoral guide, each of the condyle support platforms being smooth, the surface of each of the condyle support platforms further having a shallow concavity; and a body, the body incorporating the upper and lower surfaces, having a hollow outer portion surrounding an internal reservoir, the material of the body being impermeable to fluid; the body further having one or more ports, each having a channel, each channel extending through the hollow outer portion of the body, directing the flow of fluid in and out of the port(s). At least one channel can have features to deliver fluid from the reservoir into the synovial fluid, surrounding tissues and vascular bed, for example an opening, a membrane, a flow restrictor or diffusor. The method of delivering fluid from said spacer may include continuous or periodic osmosis, diffusion, or applying a force to the reservoir thereby generating internal pressure to affect flow through the channel, or internally pumping the fluid from the reservoir, either cyclic, periodic or continuous, through the channel into the synovial fluid, surrounding tissues and vascular bed.

BRIEF DESCRIPTION OF THE DRAWINGS

Advantages of embodiments of the present invention will be apparent from the following detailed description of the exemplary embodiments. The following detailed description should be considered in conjunction with the accompanying Figures in which:

FIG. 8 is an exemplary embodiment of an antibiotic dispensing spacer.

DETAILED DESCRIPTION

Aspects of the present invention are disclosed in the following description and related Figures directed to specific embodiments of the invention. Those skilled in the art will recognize that alternate embodiments may be devised without departing from the spirit or the scope of the claims. Additionally, well-known elements of exemplary embodiments of the invention will not be described in detail or will be omitted so as not to obscure the relevant details of the invention.

As used herein, the word "exemplary" means "serving as an example, instance or illustration." The embodiments described herein are not limiting, but rather are exemplary only. It should be understood that the described embodiments are not necessarily to be construed as preferred or advantageous over other embodiments. Moreover, the terms "embodiments of the invention", "embodiments" or "invention" do not require that all embodiments of the invention include the discussed feature, advantage or mode of operation.

This application incorporates by reference, in its entirety, U.S. patent application Ser. No. 15/178,707, filed Jun. 10, 2016. For the sake of brevity, some descriptions regarding various embodiments and figures from that application are not repeated herein.

According to at least one exemplary embodiment, and referring generally to the Figures, an antibiotic dispensing spacer to be used in an infected total knee arthroplasty revision procedure may be shown and described. The antibiotic dispensing spacer may directly introduce antibiotics into an infection site at a controlled rate that remains consistent over time and may utilize an antibiotic supply that may be replenishable without a need for surgery to remove and replace the device. The antibiotic dispensing spacer may also be shaped and configured so as not to interfere with the function of the knee joint of the patient, including achieving all wear, fatigue, and strength requirements or desired achievements for a properly functioning knee implant, whether full or empty. Such a spacer may create a new option for the treatment of periprosthetic knee infection, combining many of the benefits of the treatments of the previous options and eliminating many of the drawbacks inherent in said treatments by allowing the spacer to be retained after treatment. In other words, the spacer may be permanently implanted.

Figure 1:
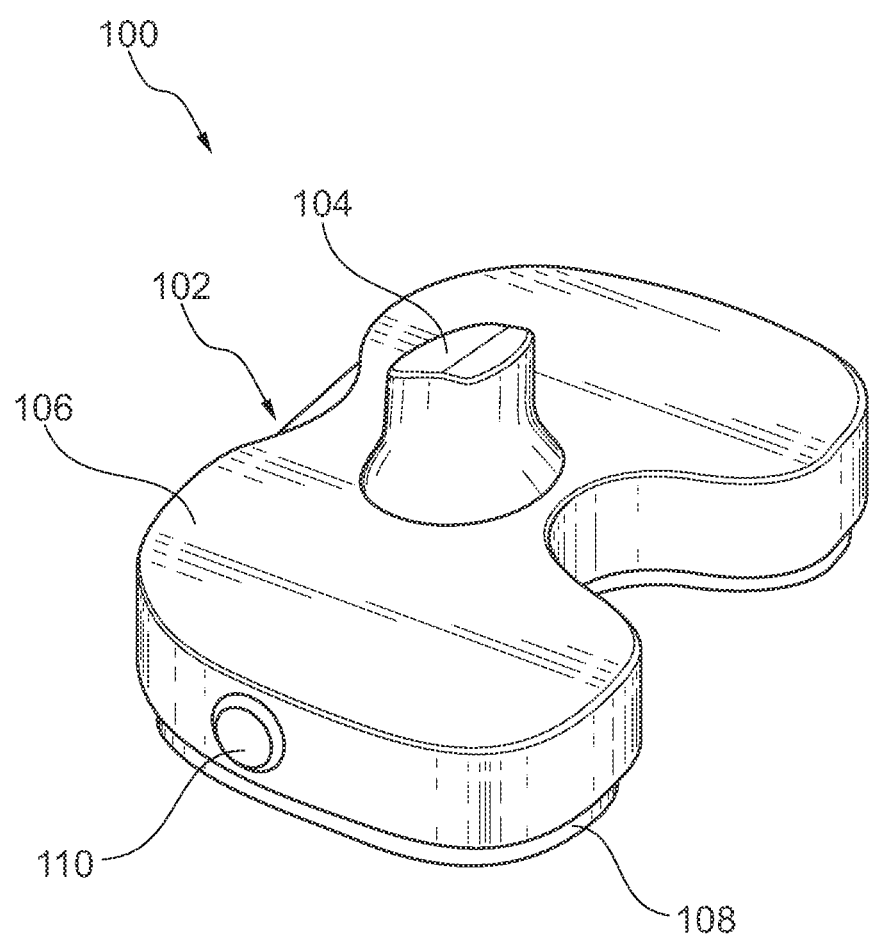
FIG. 1 is an exemplary embodiment of an antibiotic dispensing spacer.

FIG. 1 may depict an exemplary embodiment of an antibiotic dispensing spacer 100, which may be used in a total knee arthroplasty revision procedure. According to an exemplary embodiment, antibiotic dispensing spacer 100 may be adapted to fit between a typical femoral component of a knee replacement prosthesis and a typical tibial component of a knee replacement prosthesis, and may be configured to replace or be substituted for an existing spacer in either a temporary or permanent condition. According to an exemplary embodiment, antibiotic dispensing spacer 100 may fit atop a tibial component of a knee replacement prosthesis, and may be attached to the tibial component by, for example, an adhesive or a physical locking connection.

Antibiotic dispensing spacer 100 may include a hollow outer shell 102. The upper surface 106 of the antibiotic dispensing spacer 100 may be smooth, and the lower surface 108 of the antibiotic dispensing spacer 100 may include one or more attachment sites at which the antibiotic dispensing spacer 100 can be attached to a tibial component of a knee replacement prosthesis. Antibiotic dispensing spacer 100 may also include one or more ports 110 extending through the hollow outer shell 102 into one or more internal reservoirs located within the antibiotic dispensing spacer 100. Ports 110 may include, for example, a channel portion extending through the hollow outer shell 102 and a flow restrictor portion preventing the flow of fluid in and out of the hollow outer shell 102 when not desired. In some embodiments, antibiotic dispensing spacer may have an optional tibial post 104 protruding from the top of the spacer 100.

According to an exemplary embodiment, the hollow outer shell 102 of the antibiotic dispensing spacer 100 may be constructed from a material that is biocompatible, and such that there is a low coefficient of friction between the material of the antibiotic dispensing spacer 100 and the material of the femoral component of the knee replacement prosthesis that is in contact with the upper surface 106 of the antibiotic dispensing spacer 100. For example, according to an exemplary embodiment, the hollow outer shell 102 of the antibiotic dispensing spacer 100 may be constructed from a polyethylene, ultra-high molecular weight polyethylene (UHMWPE), UHMWPE with vitamin E, a poly-ether-ether-keytone, a carbon composite, or from another appropriate biocompatible material or combination of materials, as desired.

According to an exemplary embodiment, hollow outer shell 102 of the antibiotic dispensing spacer 100 may be formed in any of a variety of shapes and sizes. According to an exemplary embodiment, spacers 100 may be constructed in each of a variety of shapes and sizes, for example the shapes and sizes of the most common commercially available total knee prosthesis spacers, or the shapes and sizes of the total knee prosthesis spacers sold by a particular company. This may allow the spacers 100 to be used for different patients or for different techniques; for example, according to an exemplary embodiment, there may be spacer 100 designs that are intended to be used for posterior stabilized total knee replacement, and spacer 100 designs that are intended to be used for cruciate retaining total knee replacement, or cruciate sacrificing knee replacement, or any other types of knee replacement, as desired. Fixed-bearing spacers 100 and rotating platform/mobile bearing spacers 100, as well as any other spacer 100 designs, may also be available, as desired. According to another exemplary embodiment, spacers 100 may be modular in shape, or may be moldable or otherwise modifiable. For example, according to an exemplary embodiment, a spacer 100 may become soft and pliable after being exposed to a particular chemical or being exposed to heat and may be modifiable in such a form.

According to an exemplary embodiment, the upper surface 106 of the antibiotic dispensing spacer 100 may be smooth and may be shaped so as to accommodate a femoral component of a knee replacement prosthesis. For example, according to an exemplary embodiment, the upper surface 106 may be substantially flat or substantially curved, as desired. For example, according to an exemplary embodiment, the upper surface 106 may have two concave portions, one on either side of the antibiotic dispensing spacer 100 and separated by a tibial post 104. Each of the concave portions may be used to, for example, accommodate the condyles of the femoral component, such that each of the condyles of the femoral component fits within one of the concave portions.

According to an exemplary embodiment, an antibiotic dispensing spacer 100 may have an optional tibial post 104, which may extend upwards from the upper surface 106 of the antibiotic dispensing spacer 100. According to an exemplary embodiment, in a "posterior-stabilized" or "cruciate-substituting" prosthesis design, the tibial post 104 may be used to prevent posterior translation of the tibia on the femur, helping to stabilize the knee in the absence of the posterior cruciate ligament (PCL). This may allow the antibiotic dispensing spacer 100 to be substituted for an existing spacer of a "posterior-stabilized" or "cruciate-substituting" prosthesis. Other prosthesis variants, such as a "cruciate-retaining" prosthesis, may not include a tibial post 104, and may be used when the patient's PCL can be retained; in such a case, an antibiotic dispensing spacer 100 may be similar in structure to the spacer of a cruciate-retaining design, and may not include a tibial post 104.

According to an exemplary embodiment, the lower surface 108 of the antibiotic dispensing spacer 100 may be connectible, for example by the use of a locking mechanism, to the top portion of a tibial component of a knee replacement prosthesis (known as the "tibial tray"). According to another exemplary embodiment, features on the upper surface 106 of the antibiotic dispensing spacer 100 may be connectible, for example by the use of a locking mechanism, to the top portion of a tibial component of a knee replacement prosthesis (known as the "tibial tray").

According to an exemplary embodiment, the antibiotic dispensing spacer 100 may be of a fixed bearing or rotating platform/mobile bearing design. For example, in one exemplary embodiment, the antibiotic dispensing spacer 100 may have a fixed-bearing design; in such an embodiment, the lower surface 108 may be rigidly attached, for example by a rigid connector or an adhesive, to the tibial component of the knee replacement prosthesis. According to another exemplary embodiment, the antibiotic dispensing spacer 100 may have a rotating platform design; in such an embodiment, the lower surface 108 may be able to rotate back and forth by several degrees on the tibial component of the knee replacement prosthesis.

The hollow outer shell 102 of the antibiotic dispensing spacer 100 may contain one or more reservoirs, which may be accessible from the outside of the antibiotic dispensing spacer 100 by one or more channels and ports 110. For example, in one exemplary embodiment, the spacer 100 may have a port 110 on the anterior, medial or lateral aspects of the spacer 100 which leads to an internal reservoir. According to an exemplary embodiment, port or septum 110 may be protuberant from the surface of the spacer 100, which may, for example, facilitate palpation of the port by an administrating physician. According to another exemplary embodiment, port 110 may not be protuberant, and may instead be a window in the anterior, medial, or lateral aspect of the spacer 100; such a window-type port 110 may be flush with or sunk into the hollow outer shell 102 of a spacer 100, as desired. In still another exemplary embodiment, port 110 may be connected to a separate, subcutaneous infusion port that is implanted nearby adjacent to the skin. Port 110 and infusion port can be connected by a flexible tube.

In an embodiment, port 110 may be refilled after the spacer 100 is in place, by the application of a percutaneous needle. An administrating physician may insert the needle through the skin of the patient and into the port 110 of the spacer 100, thereby allowing access to an internal reservoir of the spacer 100 and allowing the spacer 100 to be refilled via the needle, for example with the use of a syringe. According to an exemplary embodiment, the port or septum 110 may be made of rubber or another flexible material, or alternatively may be made of a sponge or fibrous material, such that a needle can be inserted through the port 110 and into an internal reservoir without significantly compromising the ability of the port 110 to retain fluid material in the reservoir. According to another exemplary embodiment, the port 110 may be flexibly held in place by the spacer 100, such that the application of a force to the port 110, with a needle or other tool, can open the port 110 and allow for an internal reservoir of the spacer 100 to be refilled via a needle. For example, in an exemplary embodiment, the port 110 may be constructed from a hard material and may be spring-loaded or otherwise held in place by elastic material. In another exemplary embodiment, the internal reservoir may have a structure capable of retaining fluid without requiring a port 110 to act as a barrier; for example, according to an exemplary embodiment, the internal reservoir may be filled with a sponge, such as a hydrophobic or hydrophilic sponge, and fluid may be injected directly into the sponge. According to such an embodiment, port 110 may be, for example, an opening in the hollow outer shell 102 of the spacer 100 allowing insertion of a needle into the internal reservoir.

According to another exemplary embodiment, the port 110 may be connected to a catheter. Catheter may be linked to a refill mechanism, and may be connected to the reservoir of the spacer 100 by percutaneously tunneling the catheter through the soft tissue of the patient's thigh or calf to the reservoir of the spacer 100. Refill of an internal reservoir of the spacer 100 may then take place through this catheter. According to an exemplary embodiment, a catheter, or a port 110 that allows both addition of and removal of antibiotic fluid, may be used in order to allow antibiotic fluid to be drawn out of the spacer 100 as well as added to the spacer 100; this may allow for antibiotic fluid levels or concentrations in the spacer 100 to be more easily checked. Other fluids other than antibiotic fluid may also be added or removed, for example through the port 110 and/or the catheter. For example, in one exemplary embodiment, anticoagulants may be added to prevent clogging of the pores, while in another exemplary embodiment, chemical surfactants may be added to help break down biofilm on the prosthesis. In still another exemplary embodiment, therapeutic agents, such as hyaluronic acid or stem cells, may be added for delivery into the joint.

According to an exemplary embodiment, the port 110 may have a localization marking that allows the port 110 to be localized on X-ray or fluoroscopy. For example, according to an exemplary embodiment, the port 110 may be surrounded by a radiodense ring that allows the port 110 to be observed in an X-ray. According to another exemplary embodiment, such as when the port 110 is constructed from a hard material, the port 110 itself may be constructed from a radiodense material. In another exemplary embodiment, the port or septum 110 may have a magnetic material ring surrounding the septum wherein a second magnetic ring can be used on the surface of the skin to help localization of the port for injection of an antibiotic.

Figure 2:
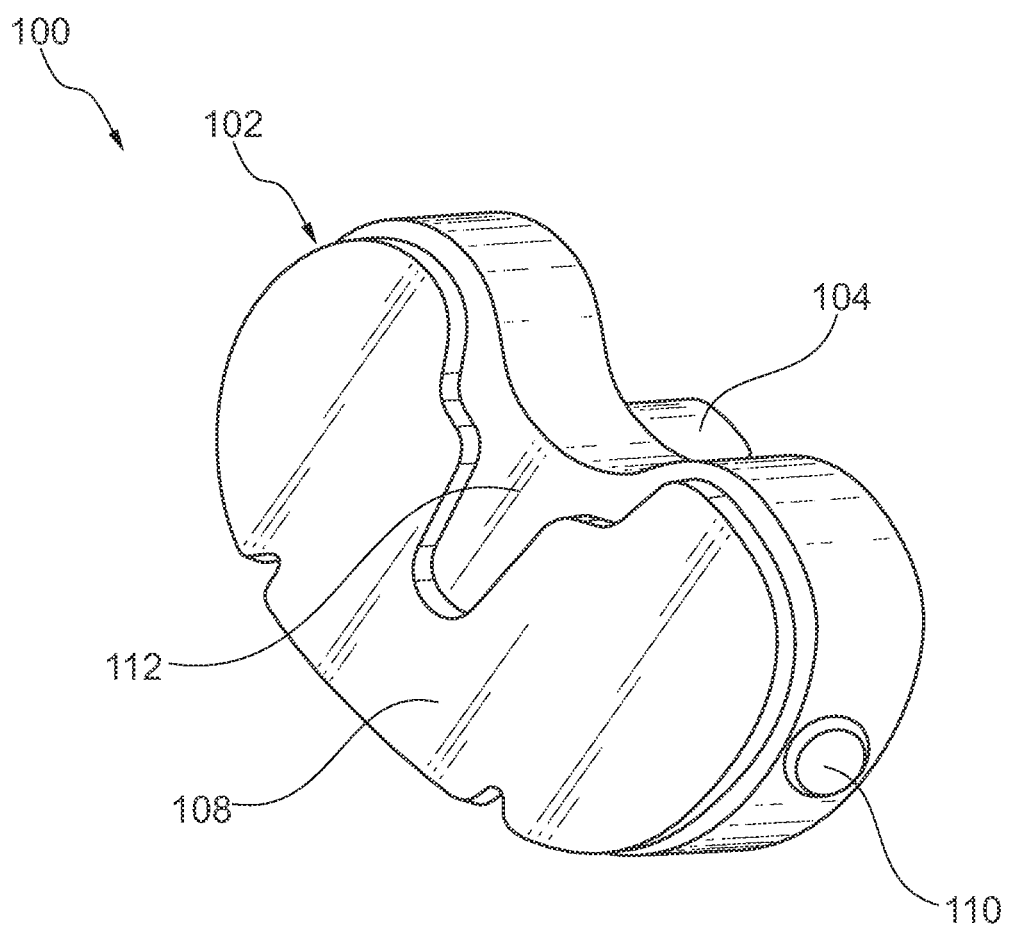
FIG. 2 is a view of the underside of an exemplary embodiment of an antibiotic dispensing spacer.

Turning now to exemplary FIG. 2, FIG. 2 shows a view of the underside of an exemplary embodiment of an antibiotic dispensing spacer 100. According to an exemplary embodiment, the lower surface 108 of the antibiotic dispensing spacer 100 may include a locking mechanism 112 or other mechanical connector by which the antibiotic dispensing spacer 100 can be connected to a tibial tray. For example, according to an exemplary embodiment, a spacer 100 may slide onto an upraised portion of the tibial tray, which may extend into and lock inside the locking mechanism 112. As previously mentioned, according to an exemplary embodiment, the antibiotic dispensing spacer 100 may be of a fixed-bearing or rotating platform/mobile bearing design. According to an exemplary embodiment, locking mechanism 112 may be a duplicate of the locking mechanisms of one or more other commercially available spacers. According to another exemplary embodiment, locking mechanism 112 may be modular or may be modifiable, such that the locking mechanism 112 can be affixed to different tibial tray models or mechanisms. In another exemplary embodiment, the antibiotic dispensing spacer 100 may be connected to a tibial tray by a non-mechanical connection, or a combination of mechanical and non-mechanical connections; for example, in an exemplary embodiment, the antibiotic dispensing spacer 100 may be connected to the tibial tray by an adhesive, by grout/bone cement, or by any other nonmechanical connection, as desired.

Figure 3:
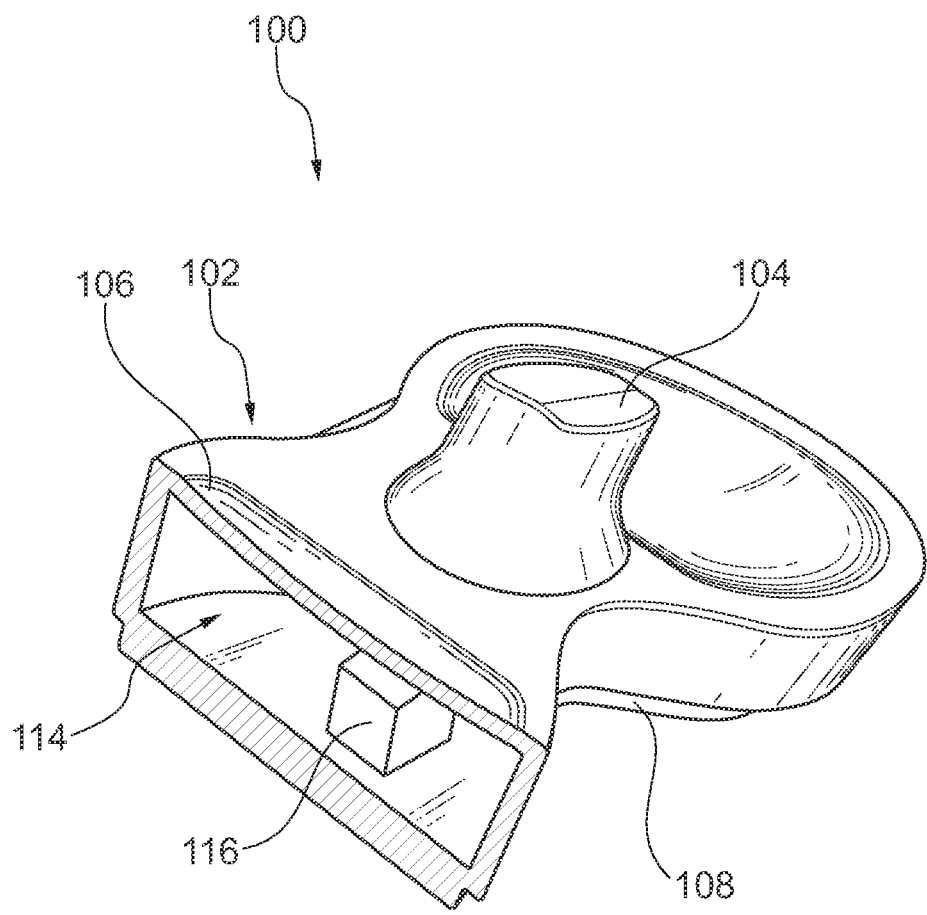
FIG. 3 is a view of the inside of an exemplary embodiment of an antibiotic dispensing spacer.

Turning now to exemplary FIG. 3, FIG. 3 shows a view of the inside of an exemplary embodiment of an antibiotic dispensing spacer 100. The internal portion of an antibiotic dispensing spacer 100 may include, within the hollow outer shell 102, one or more internal reservoirs 114. According to an exemplary embodiment, internal reservoirs 114 may be refillable from the outside; for example, internal reservoirs 114 may be refillable from a port located on the antibiotic dispensing spacer 100 and extending through the hollow outer shell 102.

According to an exemplary embodiment, the one or more internal reservoirs 114 may hold one or more fluids, which may be, for example, solutions of antibiotics, anticoagulants, surfactants, other fluids, or some combination thereof. The one or more internal reservoirs 114 may also be linked to a dispensation mechanism for the fluids, which may act to dispense the fluid in a controlled fashion. For example, according to an exemplary embodiment, the antibiotic dispensing spacer 100 may include a dispenser as one or more pumps, such as pump 116. Pump 116 may be powered by, for example a battery located within the antibiotic dispensing spacer 100 or by another power source, as desired. Pump 116 may be connected to one or more pores or portals located on the hollow outer shell 102 of the spacer 100 and may act to dispense antibiotic-containing fluid out of the one or more internal reservoirs 114 of the spacer 100. Alternatively, the dispenser, and pump 116, may be a passive dispenser designed to dispense fluids passively, for example over time or based on other measured or determined conditions.

Figure 4:
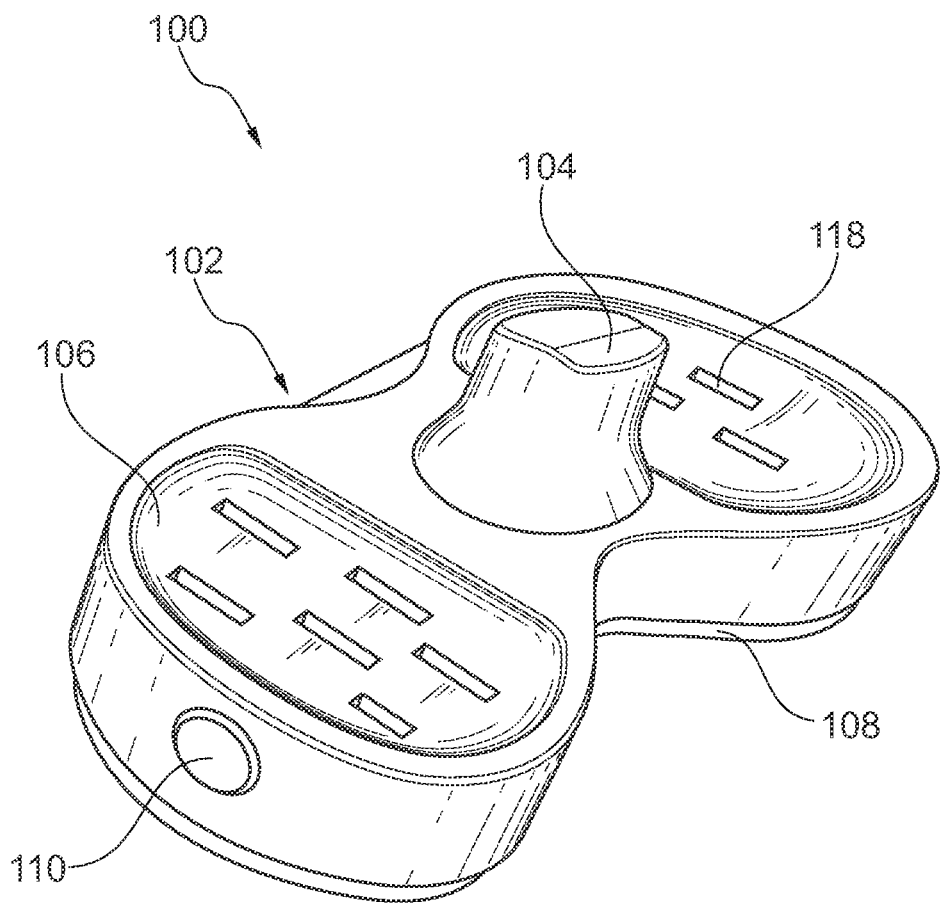
FIG. 4 is an exemplary embodiment of an antibiotic dispensing spacer having a number of pores.

Turning now to exemplary FIG. 4, FIG. 4 shows an alternative exemplary embodiment of an antibiotic dispensing spacer 100, in this case showing, visibly, a plurality of pores 118 that may be located on the hollow outer shell 102 of the spacer 100. According to an exemplary embodiment, pores 118 may allow for antibiotic-containing fluid to be dispensed from an internal reservoir of the spacer 100 by the action of a pump located within the spacer 100. According to another exemplary embodiment, the pores 118 may allow simple diffusion of a liquid located within the spacer 100 to the surrounding joint, without requiring the action of a pump to dispense liquid out of the pores 118. In some exemplary embodiments, pores 118 may be constructed from or may incorporate fluid-permeable material, such as a fluid-permeable membrane; according to such an embodiment, the fluid-permeable material may restrict the rate at which antibiotic-containing fluid is dispensed into the surrounding joint, including the rate of osmosis. In other exemplary embodiments, pores 118 may be openings in the hollow outer shell 102 of the spacer 100 that extend through the hollow outer shell 102 of the spacer 100 and into one or more internal reservoirs. Pores 118 may be any size or shape, and may be provided in any number, as desired. In some exemplary embodiments, one or more pores 118 may double as a port into which additional antibiotic-containing fluid can be injected, as desired. In some exemplary embodiments, the hollow outer shell 102 may be slightly permeable to fluid; in such embodiments, no pores may be necessary, and the slight permeability to fluid of the hollow outer shell 102 may instead be used to diffuse liquid located within the spacer 100.

Turning now to exemplary FIG. 8, FIG. 8 can illustrate features of construction including the use of an internal, structural frame to allow the spacer to achieve desired wear, fatigue and strength performance over the life of the implant, per requirements established by regulatory bodies such as the FDA, ISO, ASTM, and the like, and also assure proper prosthesis performance whether the reservoir is full or empty.

Figure 9:
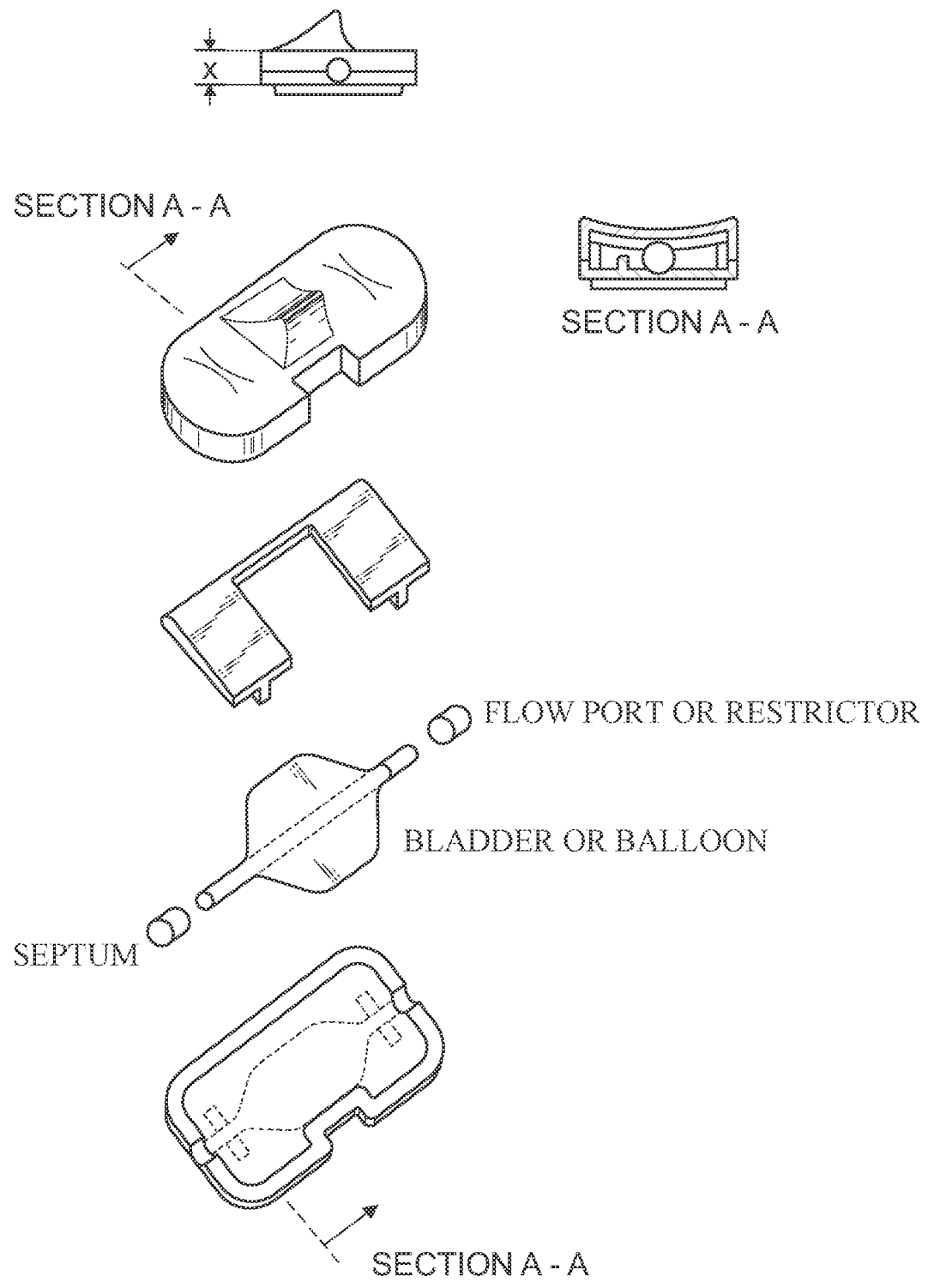
FIG. 9 is an exploded view of an antibiotic dispensing spacer illustrating a structurally supporting frame and an exemplary pumping configuration that uses an elastomeric bladder.
Figure 12:
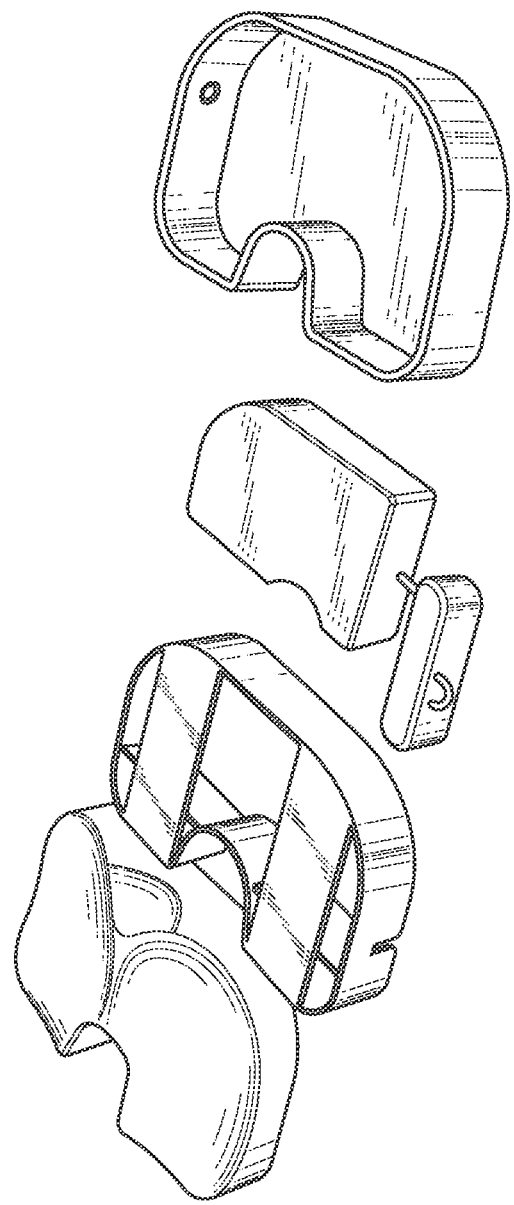
FIG. 12 is an exemplary exploded view of an antibiotic dispensing spacer illustrating a top of common spacer material, a structurally supporting internal frame, an internal pumping configuration, and a bottom of common spacer material where the top and the bottom are joined together and hold the internal components.

Turning now to exemplary FIG. 9, FIG. 9 is an exploded view of an exemplary configuration of construction wherein the upper surface forms a portion of the spacer body and the lower surface forms a portion of the spacer body. When the upper and lower portions are joined they can form the entire spacer with the proper physical features as described herein. Internal to the body is a high strength material frame that provides support for the hollow spacer such that it can meet desired mechanical performance requirements, e.g. life, wear, fatigue, strength, etc. The frame may be a separate component installed during assembly or may be integrated into the upper and/or lower halves of the body. The frame may be localized in the areas of high stress or distributed across the spacer body. The frame can remove the requirement that the hollow body must achieve all of the mechanical requirements allowing the body to be made from multiple materials. Internal to the body is a delivery or pumping mechanism. As one exemplary configuration, an elastomeric bladder can be used to hold the antibiotic under pressure. On one end there may be a port or septum attached to a channel through which the body attached to the elastomeric bladder can receive the antibiotic solution from refilling injection. On the other end can be a port or flow restricture, including an optional long length of thin, small tubing to act as a flow restricture, attached to a channel through the body attached to the elastomeric bladder to exhaust the antibiotic at a desired, known and/or regular rate. The rate may be determined in order to affect a desired antibiotic concentration in the synovial fluid, consistently above a therapeutic minimum level over the length of the treatment period. Exemplary FIG. 12 provides another view of the top and bottom shell, the high strength frame, and an exemplary internal pumping mechanism.

Figure 10:
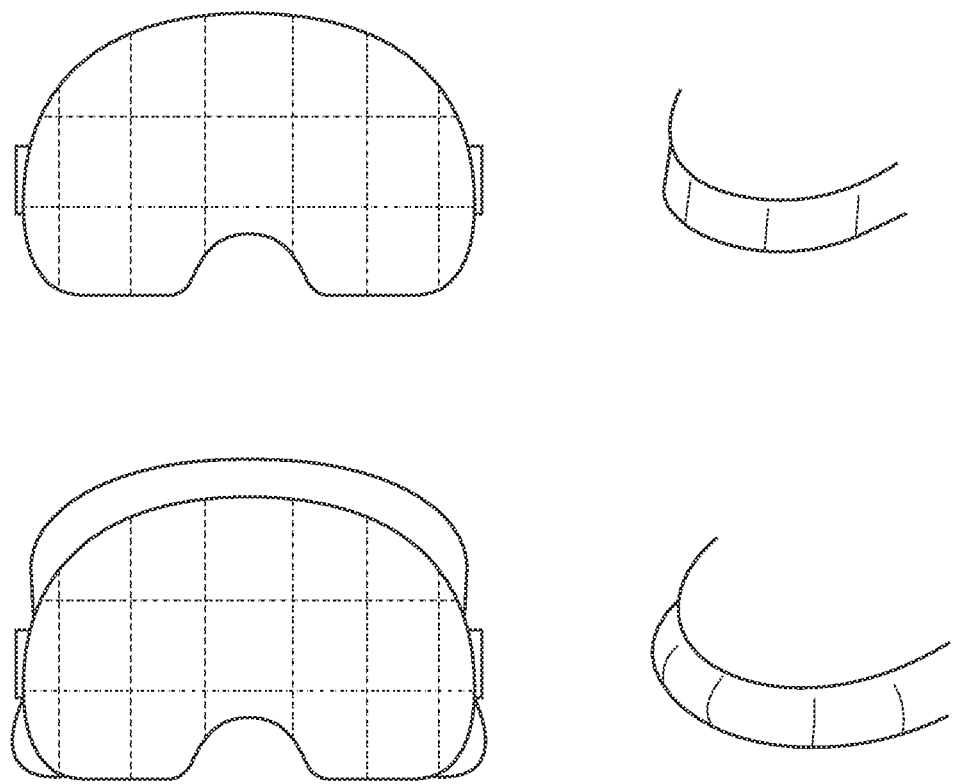
FIG. 10 is a planar view of the spacer indicating the feature of a flexible perimeter edge allowing the spacer to grow in size when filled with antibiotic and returning to its original shape when empty

Turning now to exemplary FIG. 10, FIG. 10 depicts an embodiment where the hollow body does not need to be made of a single material, given the use of an internal frame for strength and rigid materials, such as ultra-high molecular weight polyethylene (UHMWPE) for the top and bottom surfaces. In this figure, the hollow body incorporates an elastomeric material around the edge, sealed to the upper and lower surfaces, to allow the device's reservoir to expand when filled, and return to its nominal shape when empty.

As the spacer may be desired to maintain a specific height for proper prosthetic performance in a knee, the height between the tibial tray and the femoral condyles can be fixed; however the perimeter may grow in circumference a small or desired amount to provide greater internal volume of the reservoir and therefore lengthen the time between refills that are performed. In an effort to avoid the clinical impracticality of daily injections, or daily refilling of the reservoir, the reservoir can be sized to hold multiple days, up to multiple weeks, of concentrated solution. The pumping system can employ very low periodic flowrates to deliver a sufficient amount of antibiotic into the synovial fluid to maintain the minimum therapeutic concentration, consistently above the minimum level over an extended treatment period. Such flowrates may be varied, as desired.

In another exemplary embodiment, a separate, secondary reservoir may be implanted under the skin in an appropriate anatomical location nearby the spacer to provide greater antibiotic reservoir and reduce the number of times the device needs to be refilled during the treatment period. The secondary reservoir can be connected to the spacer through a short, implanted tube connected to the filling channel in the spacer. The secondary reservoir may contain the aforementioned port, including the radiopaque and magnetic ring in order to improve the percutaneous access of a needle to refill the secondary reservoir and spacer.

Figure 5:
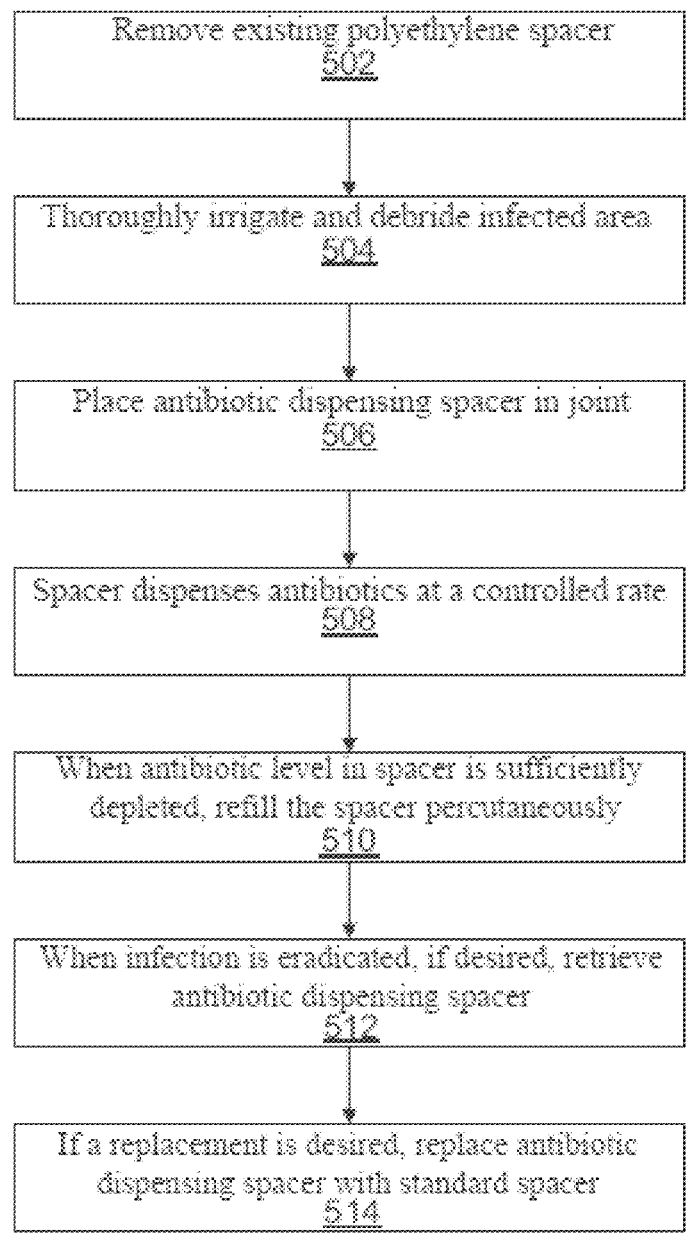
FIG. 5 is an exemplary process flow diagram depicting a method by which an antibiotic dispensing spacer may be used to treat an infection.

Turning now to exemplary FIG. 5, an exemplary process flow diagram depicting a method by which an antibiotic dispensing spacer may be used to treat an infection may be depicted. Once an infection in a total knee replacement prosthetic has been diagnosed, in a first operation, a standard polyethylene spacer may be removed from the knee replacement prosthetic 502. The infection site may then be thoroughly irrigated and debrided in order to remove infected tissue 504. Once the irrigation and debridement 504 is finished, an antibiotic dispensing spacer having one or more internal reservoirs and having a shape similar to or identical with the standard polyethylene spacer removed from the knee replacement prosthetic may be selected, and if necessary may be further reshaped. The one or more internal reservoirs of the antibiotic dispensing spacer may be filled with one or more antibiotics, and the antibiotic dispensing spacer may be put inside the knee replacement prosthetic in place of the standard polyethylene spacer 506.

Once the antibiotic dispensing spacer is put in place, it may be left in place for an extended period of time, such as about 6 weeks to 6 months or longer. The extended period can last however long it may take for the infection to be satisfactorily treated. During that time, the antibiotic dispensing spacer may dispense antibiotics, for example using a pump or using diffusion, into the knee area at a controlled and consistent rate 508 with the reservoir being refilled when necessary. Alternatively, in an exemplary embodiment, the antibiotic dispensing spacer may be left in place permanently, which may, for example, simplify the process of treating a recurrence of the infection. Alternatively, in another exemplary embodiment, the antibiotic dispensing spacer may be added preemptively, before an infection occurs, in order to simplify the process of treating the infection and reduce the need for further surgeries after the prosthesis is initially put in place. In another similar exemplary embodiment, the antibiotic dispensing spacer may be added preemptively, at the time of the primary total knee arthroplasty surgery, in order to deliver post-operative prophylactic antibiotic therapy to reduce the propensity of contracting an infection from surgery.

At one or more instances within the time period in which the antibiotic dispensing spacer is in place, the antibiotic dispensing spacer may become depleted past a desirable point. For example, the reservoirs of the antibiotic dispensing spacer may become fully depleted, or sufficiently depleted that the amount of antibiotic being dispensed by the antibiotic dispensing spacer are near a minimum desirable amount or less than a minimum desirable amount. At that point, the spacer may be refilled percutaneously 510, for example by the injection of a syringe into a port of the spacer or the insertion of a catheter into a port of the spacer. This may allow for the antibiotic dispensing spacer to be refilled without requiring the full surgical removal and replacement of the empty antibiotic dispensing spacer with a filled antibiotic dispensing spacer, which may result in easier maintenance of minimum antibiotic concentration levels in the synovial fluid, as well as greatly reduced inconvenience for the patient and reduced medical costs.

Once the infection has been deemed to be eradicated, the antibiotic dispensing spacer may be retrieved 512, and may be replaced with a standard spacer 514, if desired. Standard spacer 514 may be, for example, the spacer that was similar to that initially removed from the infected total knee replacement, or may be another spacer, as desired. Alternatively, as mentioned, the antibiotic dispensing spacer, depleted of any delivery solution, may be left in place permanently.

Figure 11:
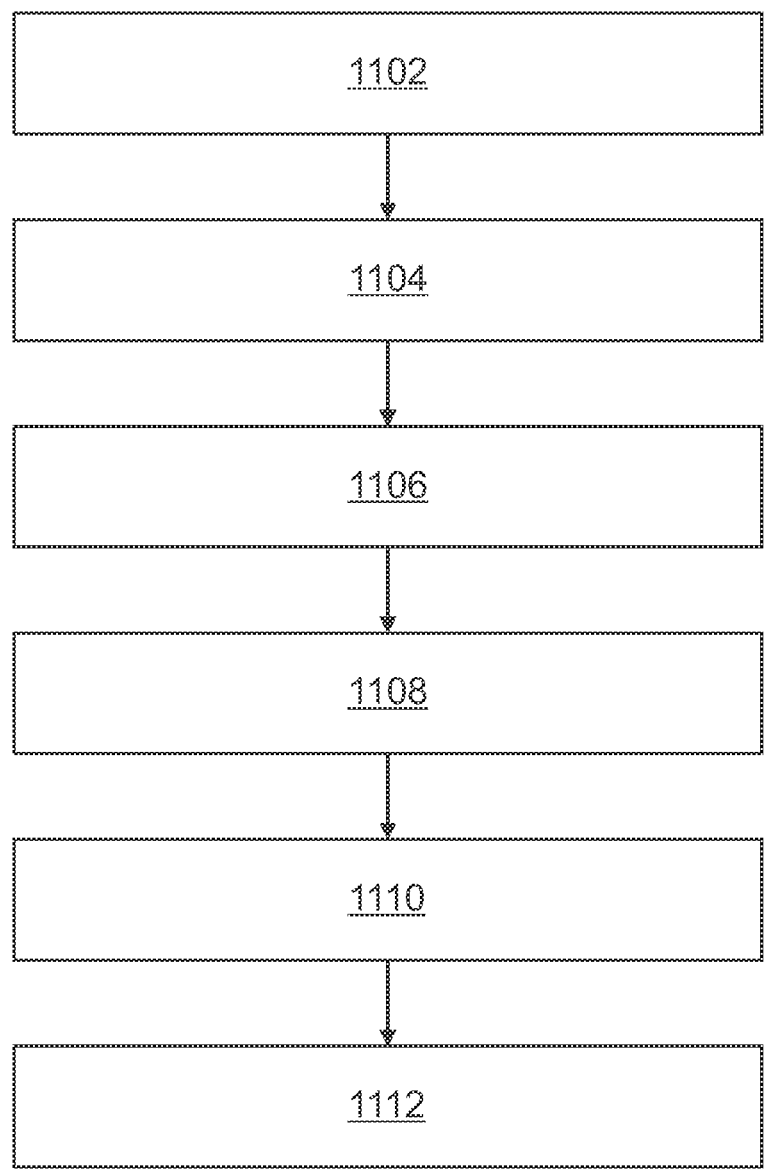
FIG. 11 is an exemplary process flow diagram depicting a method by which an antibiotic dispensing spacer may be used in a substantially permanent manner to treat an infection, where the spacer may not be removed.

Turning now to exemplary FIG. 11, another exemplary process flow diagram, once a polyethylene spacer has been removed 1102, the infected area may then be thoroughly irrigated and debrided 1104. Once the irrigation and debridement 1104 is finished, an antibiotic dispensing spacer may be put in joint 1106, and the antibiotic dispensing spacer may dispense antibiotics at a controlled rate 1108. It may be appreciated that when the antibiotic dispensing spacer has become depleted, the spacer has been refilled percutaneously 1110 and the infection has been deemed to be eradicated, the antibiotic treatment is stopped 1112. However, the spacer is not removed. No additional surgery is required or needed as the spacer conforms to all mechanical, wear, fatigue and strength requirements of the original spacer and suitable to be retained.

Figure 6:
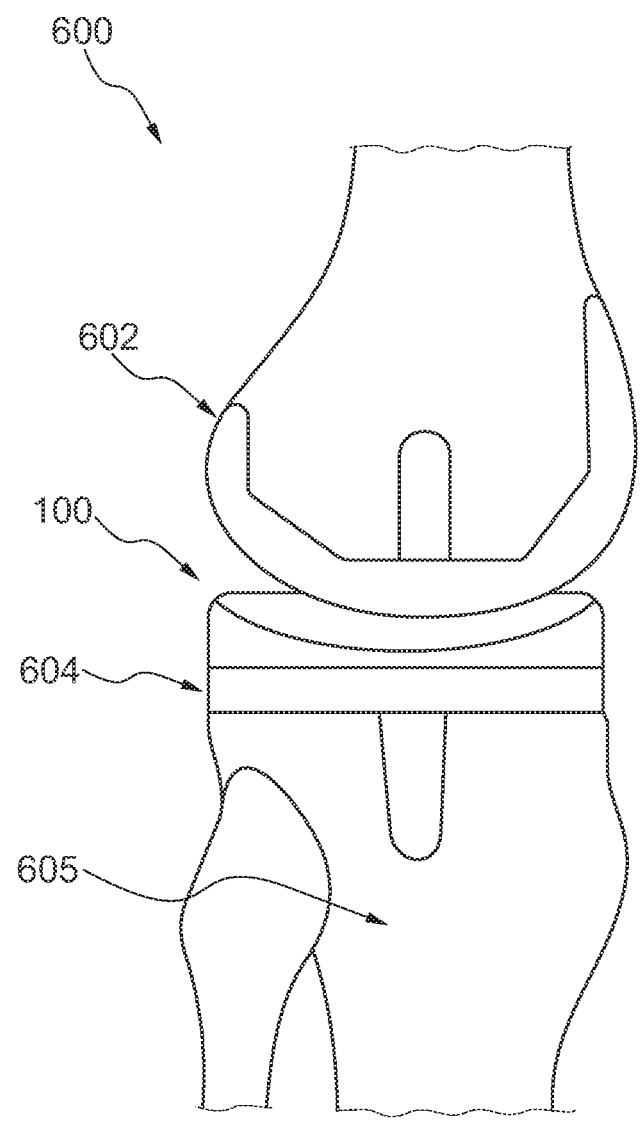
FIG. 6 is an exemplary embodiment of a total knee replacement prosthesis incorporating an antibiotic dispensing spacer.
Figure 7:
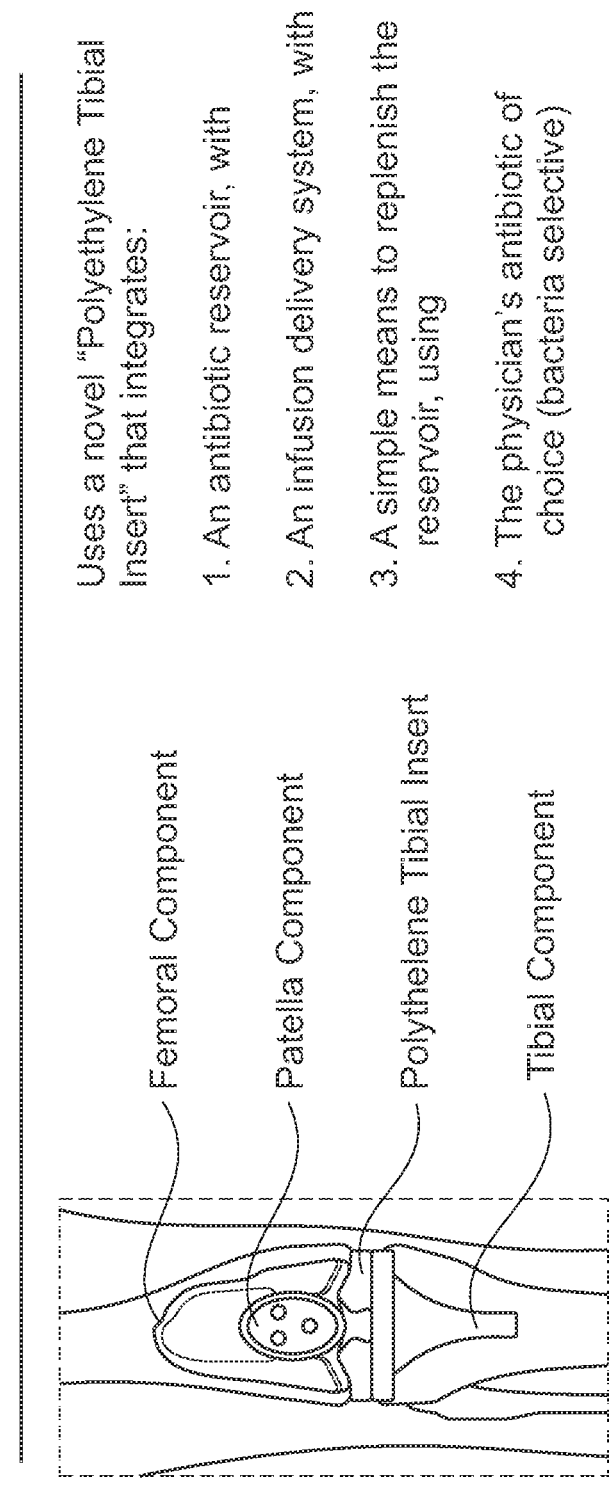
FIG. 7 is a view of a typical total knee arthroplasty implant highlighting each of the major components and the location of the spacer.

Turning now to exemplary FIG. 6, an exemplary embodiment of a total knee replacement prosthesis 600 incorporating an antibiotic dispensing spacer 100 may be provided.

Total knee replacement prosthesis 600 may have a femoral component 602, a tibial component 604, and a spacer 100, which may be an antibiotic dispensing spacer 100. According to an exemplary embodiment, spacer 100 may be connected to the tibial component 604; for example, the spacer 100 may slide onto the tibial component 604 and may lock at a locking mechanism. Alternatively, the spacer 100 and tibial component 604 may be connected by another mechanical connector or non-mechanical connection, or combination of connectors or connections, as desired. Alternatively, the lower surface of the spacer 100 may be bonded, cemented, grouted directly to the tibia 605 without a tibial tray 604, as desired. The femoral component 602 and spacer 100 may then articulate with each other, with the specifics of the articulation being dependent on the type of prosthesis used. For example, in a "posteriorstabilized" design, the tibial post of the spacer 100 may fit between the condyles of the femoral component in a rectangular box-like opening, and may slide back and forth in this opening as the tibial 604 and femoral 602 component rotate relative to one another. In another exemplary embodiment, such as in a "cruciate-retaining" prosthesis, the femoral component 602 may rest in and rotate on concave portions of the spacer 100, and may be constrained by the patient's own ligaments rather than a tibial post. In some exemplary embodiments, femoral component 602 and tibial component 604 may be constrained or hingedly connected to each other by a pin, or another mechanism, as desired.

The foregoing description and accompanying figures illustrate the principles, preferred embodiments and modes of operation of the invention. However, the invention should not be construed as being limited to the particular embodiments discussed above. Additional variations of the embodiments discussed above will be appreciated by those skilled in the art.

Therefore, the above-described embodiments should be regarded as illustrative rather than restrictive. Accordingly, it should be appreciated that variations to those embodiments can be made by those skilled in the art without departing from the scope of the invention as defined by the following claims.

What is claimed is:

1. An antibiotic spacer that provides therapeutic treatment in a knee, comprising:
    a top;
    a bottom;
    a body;
    a reservoir; and
    a dispenser;
    wherein the reservoir has an elastomeric and sealable material which allows the reservoir to hold an antibiotic under pressure, expand when filled, and return to a nominal shape when empty, and the body further comprises one or more ports, each of the one or more ports has a channel, and each channel extends through a hollow outer portion of the body to direct flow of fluid into and out of the ports; and each channel further comprises at least one of a flow restrictor and a diffuser.

2. The antibiotic spacer of claim 1, wherein the body comprises an internal frame, an upper surface, and a lower surface.

3. The antibiotic spacer of claim 2, wherein the bottom further comprises a locking element configured to slide the antibiotic spacer into receiving members of a tibial tray.

4. The antibiotic spacer of claim 3, wherein an upper surface further comprises a femoral guide and a pair of condyle support platforms.

5. The antibiotic spacer of claim 4, wherein each condyle support platform of the pair of condyle support platforms is disposed on an opposite lateral side of the femoral guide and the condyle support platforms are formed with shallow concavity.

6. The antibiotic spacer of claim 1, wherein the reservoir is disposed along a perimeter of the body and further wherein at least portions of the body are hollow and flexible and expand when the reservoir is filled.

7. The antibiotic spacer of claim 1, wherein the reservoir further comprises at least one of a septum and a filling tube.

\* \* \* \* \*